US00PP07932P

United States Patent [19]

Marciel

[11] Patent Number: Plant 7,932

[45] Date of Patent: Aug. 11, 1992

[54] ROSE PLANT NAMED DEVROUGE

[75] Inventor: Stanley G. Marciel, Aptos, Calif.

[73] Assignee: DeVor Nurseries, Inc., Watsonville, Calif.

[21] Appl. No.: 653,909

[22] Filed: Feb. 12, 1991

[51] Int. Cl.[5] ..... A01H 5/00

[52] U.S. Cl. ..... Plt./21

[58] Field of Search ..... Plt. 20, 21

*Primary Examiner*—James R. Feyrer

[57] ABSTRACT

A new and distinct greenhouse rose plant particularly distinguished by its continuous and profuse production of large flowers having a solid currant red coloration. The long lasting flowers are borne singly on sturdy stems of medium length on a vigorous, upright plant of about 140 cm. in height.

1 Drawing Sheet

BACKGROUND OF THE INVENTION

This new rose plant originated as a seedling hybrid produced by my crossing the variety Visa (U.S. Plant Pat. No. 3,452) with pollen of Forever Yours (U.S. Plant Pat. No. 2,443) at my nursery at Pleasanton, Calif. Because of the large dark red blooms of this plant and its sturdy and upright growth habit, I decided that this plant was an ideal subject for propagation testing. Test for commercial suitability and homogeneity in large scale propagation was done under my direction by budding at my nursery in Wasco, Calif. This was done through several generations which demonstrated satisfactorily that the novel characteristics of this new plant would hold true from generation to generation and appeared to be firmly fixed.

DESCRIPTION OF THE DRAWING

My new rose plant is illustrated by the accompanying full color photographic drawing which shows a face view of a fully opened flower, the colors shown being as nearly true to those herein specified as is reasonably possible to obtain by conventional photographic procedures.

DESCRIPTION OF THE NEW VARIETY

The following is a detailed description of my new rose plant based upon observation of plants grown in greenhouse at Wasco, Calif., with the color designations specified herein being according to The R.H.S. Colour Chart published by The Royal Horticultural Society of London, England.

THE PLANT

Origin: Seedling.

Parentage:

*Seed parent.*—Visa, U.S. Plant Pat. No. 3,452.

*Pollen parent.*—Forever Yours, U.S. Plant Pat. No. 2,443.

Classification:

*Botanic.*—Hybrid tea.

*Commercial.*—Greenhouse rose.

Form: A tall, upright rose bush.

Height: Approximately 140 cm. high.

Growth habit: Very sturdy, vigorous and upright.

Main stem:

*Length.*—About 52 to 58 cm. from the last flower cut.

*Color.*—Gray brown, 199-A.

*Branching character.*—Free branching.

Foliage:

*Quantity.*—Abundant.

*Number of Leaves.*—About 9 or 10 from the last flower cut.

*Size.*—About 113 mm. long.

Leaflets:

*Number.*—3 or 5.

*Shape.*—Ovate with denticulate margin.

*Size.*—About 58 mm. long by 34 mm. wide.

*Texture.*—Leathery.

*Aspect.*—Smooth and glossy.

*Color.*—Upper side — Yellow green 147-A. Under side — Gray green 189-A.

Stipules: Hairy adnate.

Rachis length: About 89 mm. on leaf having 5 leaflets; about 56 mm. on leaf having 3 leaflets.

*Petioles length.*—About 24 mm. on leaf having 5 leaflets; about 8 mm. on leaf having 3 leaflets.

Ribs and veins: Slightly grooved on top and slightly rounded underneath.

Thorns:

*Size.*—Declining and varying in size,

*Color.*—Yellow green 152-B with tips of gray red 182-C.

THE BUD

Size: Medium.

*Diameter.*—About 28 mm.

*Length.*—About 40 mm.

Shape: Pointed and tapering.

Rate of opening: Slow.

Color of petals:

*When sepals first divide.*—Greyed purple 185-A

When petals begin to unfurl.—Red 53-A.

Sepals:

*Number.*—Five.

*Shape.*—Spreading with small leafs protruding.

*Character.*—Branched and curling back when flowers open.

*Color.*—Inside — Yellow-Green 148-D. Outside — Yellow-Green 144-A.

Calyx:

*Shape.*—Funnel shaped.

*Size.*—Large.

*Splitting.*—Calyx does not split.

*Aspect.*—Smooth.

Flower stem:

*Length.*—About 85-103 mm.

*Character.*—Slender and erect with sparse, small spines.

*Color.*—Yellow-Green 144-A.

THE FLOWER

Blooming habit: Continuous and profuse from early Spring through mid-season and Fall, blooming freely under greenhouse conditions.

Size of bloom: Large.

*Diameter.*—About 110 mm. when ¾ open.

*Depth.*—About 55 mm.

Borne: Singly on strong, upright stem.

Shape:

*When bloom first opens.*—Cup shaped with a high center.

*When bloom matures.*—The petals become nicely imbricated and cupped.

Petalage:

*Number of petals.*—About 24.

*Arrangement.*—Imbricated.

*Form.*—With slightly, curled under margins.

*Texture.*—Leathery, but soft.

*Appearance.*—Velvety.

*Color.*—Outer petals — 46-A with base of Green Yellow 1-C. Reverse side — Red 53-B with base of Yellow 4-B. Inside petals — Greyed Purple 185-A with base of Yellow 3-C. Reverse side — Greyed Purple 187-C with base of Yellow 4-C.

Petaloids:

*Number.*—About 4 to 7.

*Size.*—About 20 mm. long by 11 mm. wide.

*Color.*—Greyed Purple 187-A with a base of Yellow 4-C.

Flower Stem:

*Length.*—About 85 to 103 mm.

*Color.*—Yellow Green 14-A.

*Character.*—Very sturdy and upright.

Fragrance: Strong musk fragrance.

Persistence: In greenhouse environment, flower hangs on and dries.

Disease resistance: Resistant to mildew, rust and black spot, as observed at Wasco, Calif.

Discoloration after full bloom: Discolors to Red Purple 60-A.

THE REPRODUCTIVE ORGANS

Stamens:

*Number.*—About 160–170.

*Arrangement.*—Antrorse.

*Anthers.*—Size: About 3 mm. Color: Yellow Orange 22-C.

Filaments:

*Length.*—About 8 mm.

*Color.*—Red 50-B.

Pollen:

*Color.*—Yellow orange 22-C.

Pistils:

*Number.*—About 115 to 119.

*Styles.*—Length: About 9 to 11 mm. Color: Yellow Green 154-D with Red 39-B near the top.

Stigmas:

*Color.*—Yellow Orange 14-D.

Character of the ovaries: Oblong, and rounded with small silvery hairs.

Fruit:

*Fertility.*—The fruit is fertile.

*Shape.*—Round.

*Color.*—Orange 26-A.

I claim:

1. A new and distinct variety of rose plant, substantially as herein shown and described, characterized by its profuse and continuous production of large clear and dark red flowers which are borne on very sturdy upright stems.

* * * * *

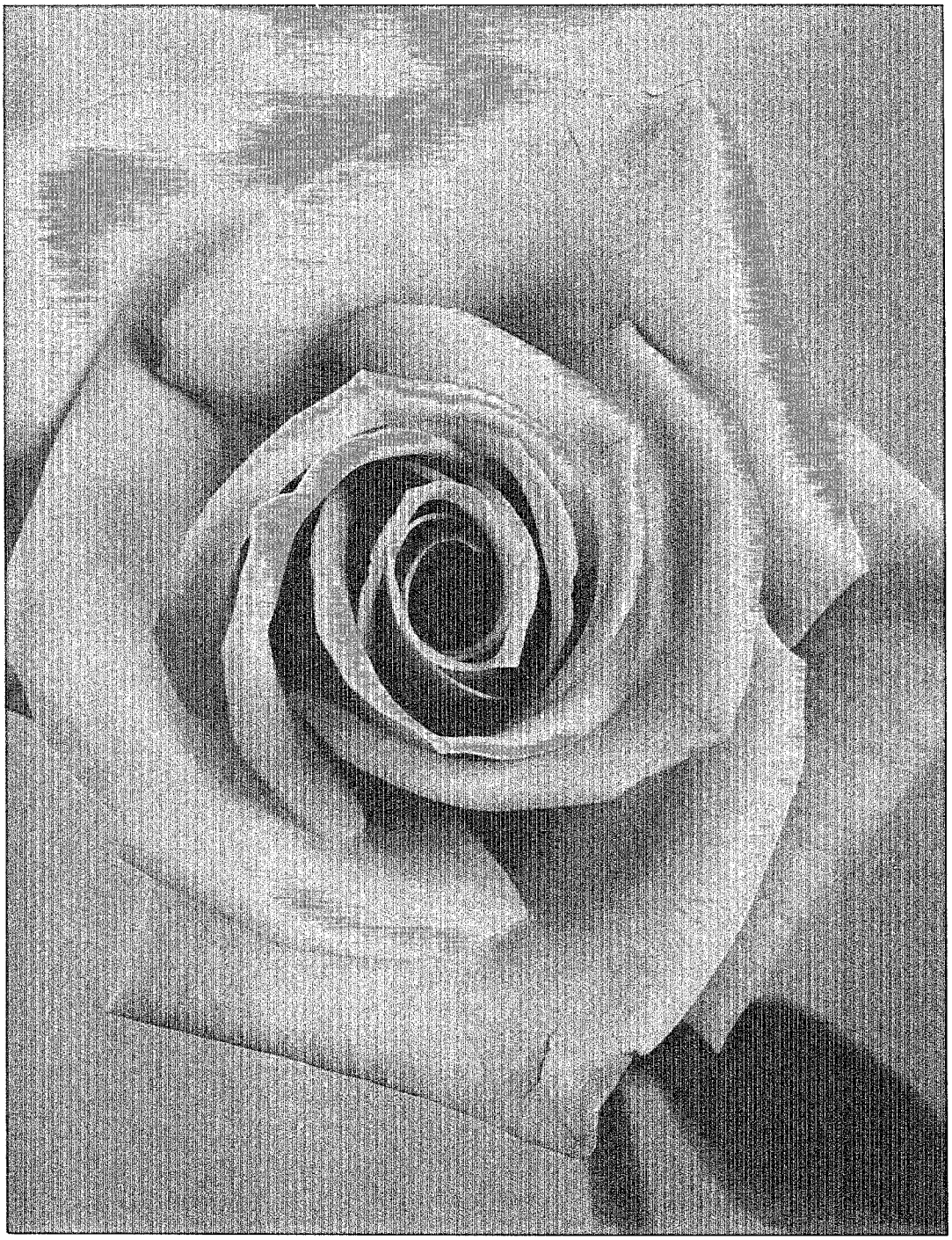

UNITED STATES PATENT AND TRADEMARK OFFICE

CERTIFICATE OF CORRECTION

PATENT NO. : Plant 7,932

DATED : August 11, 1992

INVENTOR(S) : Stanley G. Marciel

It is certified that error appears in the above-identified patent and that said Letters Patent is hereby corrected as shown below:

On the title page, Col 1, line 1, delete "Invention" and insert
--New Plant--

Signed and Sealed this

Twenty-first Day of September, 1993

Bruce Lehman

*Attest:*

BRUCE LEHMAN

*Attesting Officer*

*Commissioner of Patents and Trademarks*